(12) United States Patent
Yoshimura et al.

(10) Patent No.: US 6,673,629 B2
(45) Date of Patent: *Jan. 6, 2004

(54) NEUTRALIZATION OF POLYCATIONS IN A CHROMATOGRAPHIC DEVICE FOR WHOLE BLOOD USE

(75) Inventors: Toru Yoshimura, Matsudo (JP); Toshihiro Ogasawara, Chiba (JP); Michihiro Saito, Kashiwa (JP); John P. Groff, Gurnee, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/007,651

(22) Filed: Jan. 15, 1998

(65) Prior Publication Data

US 2001/0006823 A1 Jul. 5, 2001

(51) Int. Cl.[7] .............................................. G01N 33/533
(52) U.S. Cl. .......................... 436/518; 422/56; 422/57; 422/58; 422/59; 422/61; 422/101; 435/7.1; 435/7.94; 435/287.7; 435/287.8; 435/287.9; 435/962; 436/520; 436/521; 436/541; 436/15; 436/16; 436/824; 436/825; 530/380
(58) Field of Search .................... 422/56–61, 101; 435/7.1, 7.94, 287.7, 287.8, 287.9, 962; 436/518, 520, 521, 541, 15, 16, 824, 825; 530/380

(56) References Cited

U.S. PATENT DOCUMENTS

| 4,308,232 A | * | 12/1981 | Crouther et al. |
| 4,477,575 A | * | 10/1984 | Vogel et al. |
| 4,594,327 A | | 6/1986 | Zuk |
| 4,678,757 A | * | 7/1987 | Rapkin et al. |
| 4,753,776 A | | 6/1988 | Hillman et al. |
| 4,806,311 A | * | 2/1989 | Greenquist |
| 4,933,092 A | | 6/1990 | Aunet et al. |
| 4,935,147 A | * | 6/1990 | Ullman et al. |
| 5,120,643 A | | 6/1992 | Ching et al. |
| 5,186,843 A | * | 2/1993 | Baumgardner et al. |
| 5,212,060 A | | 5/1993 | Maddox |
| 5,306,623 A | * | 4/1994 | Kiser et al. |
| 5,314,803 A | * | 5/1994 | Wilk et al. |
| 5,435,970 A | * | 7/1995 | Mamenta et al. |
| 5,459,078 A | * | 10/1995 | Kline et al. |
| 5,459,080 A | * | 10/1995 | Adamczyk et al. |
| 5,547,576 A | * | 8/1996 | Onishi et al. |
| 5,654,162 A | | 8/1997 | Guire et al. |
| 5,670,381 A | | 9/1997 | Jou et al. |
| 5,753,497 A | * | 5/1998 | Bernstein et al. |

FOREIGN PATENT DOCUMENTS

| EP | 0 325 413 | 7/1989 |
| EP | 0 735 369 | 2/1996 |
| WO | 96 31270 | 10/1996 |

OTHER PUBLICATIONS

A. Katchalsky et al., Biochimica et Biophysica ACTA, vol. 33: 120–138 (1959).

* cited by examiner

Primary Examiner—Bao-Thuy L. Nguyen
(74) Attorney, Agent, or Firm—Regina M. Anderson

(57) ABSTRACT

A chromatography assay device and method for use with whole blood samples utilizing a red blood cell separating agent to aggregate red blood cells and permit plasma or serum to flow by capillary action and a neutralizing agent to neutralize any effects the red blood cell separating agent may have on the device and method.

17 Claims, 1 Drawing Sheet

NEUTRALIZATION OF POLYCATIONS IN A CHROMATOGRAPHIC DEVICE FOR WHOLE BLOOD USE

TECHNICAL FIELD OF THE INVENTION

The present invention relates to chromatography assay devices and a method of detecting an analyte in a whole blood sample, and more particularly to a device and method employing a red blood cell separating agent to aggregate red blood cells, and a neutralizing agent to neutralize any negative effect the red blood cell separating agent may have on the assay system.

BACKGROUND OF THE INVENTION

Modern clinical diagnostic methods are routinely carried out on blood samples. Unfortunately, red blood cells interfere with many diagnostic determinations. In assays for an analyte, red blood cells may inhibit binding between specific binding pair members. Likewise, red blood cells have enzyme activity which, depending on the assay employed, may interfere with the signal produced. Further, in a rapid test format using a chromatography assay device, particularly a chromatography immunoassay device, red blood cells may inhibit fluid flow which is necessary for reactions to occur on the device. For these reason and others, many assay methodologies are carried out on plasma or serum which must first be separated from a whole blood sample.

Many known techniques exist for separating red blood cells from plasma in a whole blood sample. Centrifugation is a well known method in the art by which plasma (before clotting) and serum (after clotting) is separated from whole blood. In this procedure, red blood cells settle at the bottom of the test tube, and the serum is separated by decantation or some other method. Stratifying whole blood by centrifugation, however, has many disadvantages. Generally, centrifugation requires a large blood sample to be drawn. Further, the process is time consuming and requires cumbersome laboratory equipment often not maintained in a physician's office. Finally, the extra handling of the blood increases the exposure to the potential hazards of blood-borne pathogens.

To reduce or eliminate the need for centrifugation, assay devices have been developed which employ gradient membranes or trapping membranes to separate red blood cells from the liquid portion of the blood. Immobilized anti-red blood cell antibodies have also been used.

Other known techniques for separating red blood cells from plasma or serum include (1) combining a whole blood sample with a red blood cell binding agent filtering the mixture through a solid bibulous element to which is bound at least one specific binding pair member to remove the agglutinated red blood cells; (2) passing whole blood through a glass microfiber filter which may or may not have an agglutinating agent incorporated; (3) employing a barrier or exclusion layer of polysaccharide material to prevent red blood cells from passing through and interfering with detection or visualization of a signal on a dry test strip; and (4) using a support having a polycationic surface which binds red blood cells but not plasma.

Many of these techniques for the separation of red blood cells from plasma are costly, complicated, may result in incomplete separation of red blood cells, and may cause hemolysis. Hemolysis leads to non-specific binding or high backgrounds causing a loss in assay sensitivity. This can be the result of free hemoglobin which can color the detection zone such that the zone can obtain a color that ranges from pink to dark maroon. As a result, the production of a visual chemical signal can be wholly or partly obscured by the presence of the hemoglobin color in the detection zone. Further, the use of a separating agent, such as a polycation, in an assay system tends to interfere with the system, often by aggregating other reagents or binding members in addition to the red blood cells.

Accordingly, need exists for a device and method for detecting an analyte in a blood sample without adversely effecting the assay system. Such device and method should be suitable for whole blood samples of various sizes, including small samples.

SUMMARY OF THE INVENTION

The present invention relates to a chromatography device comprising a chromatography carrier which defines a path for fluid flow capable of supporting capillary flow, an application site for said blood sample in fluid flow contact with the chromatography carrier, a detection site on the chromatography carrier spaced apart from the application site, a diffusively bound labeled substance located downstream of the application site, a diffusively bound red blood cell separating agent for separating plasma or serum from the blood sample upstream of the detection site, and a diffusively bound neutralizing agent capable of binding with the separating agent downstream of the bound separating agent and upstream of said detection site whereby a positive charge of said separating agent is neutralized. Preferably, the red blood cell separating agent is located at the application site so that the red blood cells will be separated from the serum or plasma before the serum or plasma moves down the chromatography carrier.

The present invention is also directed to a method for detecting the presence of an analyte in a sample, preferably a blood sample, which comprises providing a chromatography carrier which defines a path for fluid flow capable of supporting capillary flow, along which are (a) an application site for the blood sample in fluid flow contact with said chromatography carrier, (b) a detection site on the chromatography carrier spaced apart from the application site, (c) a diffusively bound labeled substance located downstream of the application site, (d) a diffusively bound red blood cell separating agent for separating plasma or serum from said blood sample upstream of the detection site, and (e) a diffusively bound neutralizing agent capable of binding with the separating agent located downstream of the bound separating agent and upstream of the detection site whereby a positive charge of the separating agent is neutralized; contacting the application site with the blood sample such that the red blood cell separating agent separates the plasma or serum from the blood sample, and the neutralizing agent neutralizes the positive charge of the separating agent as the sample flows along the flow path; and detecting the presence of analyte in the blood sample.

DETAILED DESCRIPTION OF THE INVENTION

Figure 1:
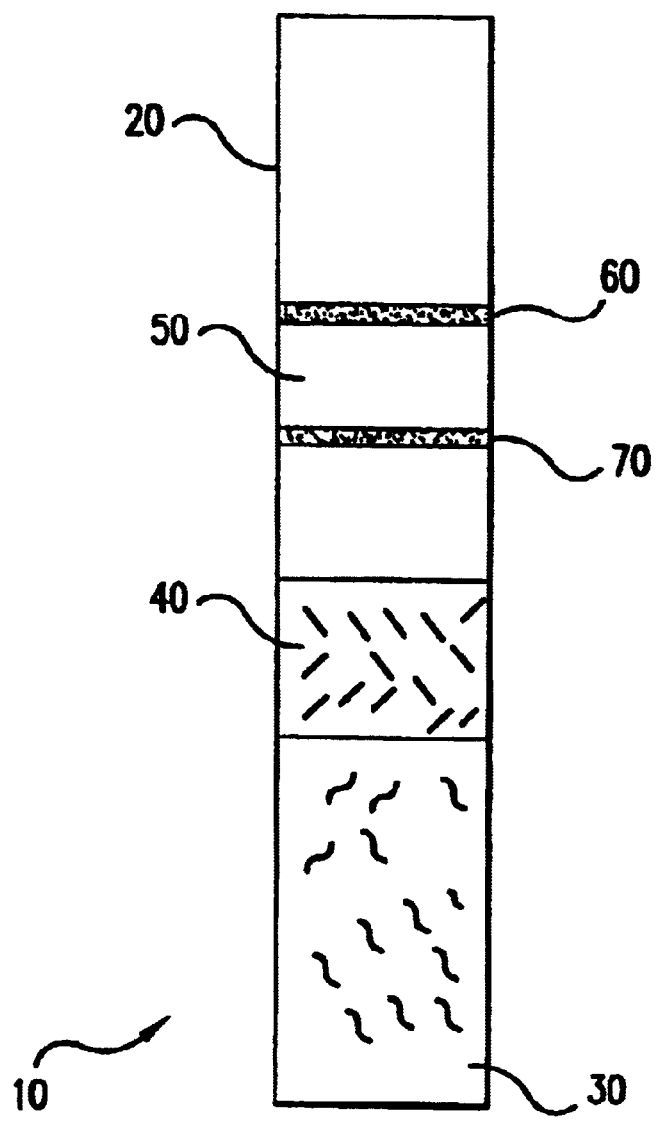
FIG. 1 depicts a preferred embodiment of the chromatography assay device of the present invention.

The present invention is based on the observation that red blood cells in whole blood samples interfere with determinations of the presence or amount of analyte in a blood sample which might otherwise be readily made via assay systems. For example, in an immunoassay, a whole blood sample contacted with an application site is unlikely to move down the strip via capillary action due to the hindering or interfering presence of the red blood cells. The present invention overcomes this problem without interfering with the sensitivity of the assay system.

The following definitions may be useful in understanding the embodiments of the present invention "Analyte" or "analyte of interest" refers to the compound or the composition to be detected or measured, which has at least one epitope or binding site. The analyte can be any substance for which there exists a naturally occurring analyte-specific binding member or for which an analyte-specific binding member can be prepared. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), and metabolites of or antibodies to any of the above substances. The term "analyte" also includes any antigenic substances, haptens, antibodies, macromolecules and combinations thereof.

"Chromatographic carrier" refers to any suitable porous, absorbent, bibulous, isotropic or capillary material, which includes the detection site of the device and through which the analyte or test sample can be transported by capillary or wicking action. It will be appreciated by one skilled in the art that the chromatography carrier can be made of a single material or more than one material (e.g., different zones, portions, layers, areas or sites can be made of different materials) so long as the multiple layers are in fluid flow contact with one another thereby enabling the passage of test sample between the materials. Fluid flow contact permits the passage of at least some components of the sample, i.e. analyte, between the zones of the porous material and is preferably uniform along the contact interface between the different zones. Natural, synthetic, or naturally occurring materials that are synthetically modified, can be used as the chromatography carrier and include, but are not limited to: paper (fibrous), or membranes (microporous) of cellulose materials such as paper; cellulose and cellulose derivatives such as cellulose acetate and nitrocellulose; fiberglass; cloth, both naturally occurring (e.g. cotton) and synthetic (e.g. nylon); porous gels; and the like.

"Label" refers to any substance which is capable of producing a signal that is detectable by visual or instrumental means. Various labels suitable for use in the present invention include labels which produce signals through either chemical or physical means. Examples include enzymes and substrates, chromagens, fluorescent compounds, chemiluminescent compounds, colored or colorable organic polymer latex particles, and liposomes or other vesicles containing directly visible substances. Preferably, radioactive labels, colloidal metallic particles or colloidal non-metallic particles are employed in the present invention. Preferred labels include colloidal gold and latex particles.

"Labeled substance" or "conjugate" refers to a substance comprising a detectable label attached to a specific binding member. The attachment may be covalent or non-covalent binding, and may include nucleic acid hybridization. The label allows the labeled substance to produce a detectable signal that is directly or indirectly related to the amount of analyte in a test sample. The specific binding member component of the labeled substance is selected to bind directly or indirectly to the analyte.

"Specific binding member" refers to a member of a specific binding pair, i.e. two different molecules wherein one of the molecules specifically binds to the second molecule through chemical or physical means. If the specific binding member is an immunoreactant it can be, for example, an antibody, antigen, hapten, or complex thereof, and if an antibody is used, it can be a monoclonal or polyclonal antibody, a recombinant protein or antibody, a chimeric antibody, a mixture(s) or fragment(s) thereof, as well as a mixture of an antibody and other specific binding members. Specific examples of specific binding members include biotin and avidin, an antibody and its corresponding antigen (both having no relation to a sample to be assayed), a single stranded nucleic acid and its complement, and the like.

"Trapping substance" refers to one or more specific binding members that are attached within or upon a portion of the chromatographic carrier to form one or more "capture sites" wherein the analyte, labeled reagent, and/or control reagent become immobilized on the chromatography carrier. The method of attachment is not critical to the present invention. The trapping substance facilitates the observation of the detectable signal by substantially separating the analyte and/or the labeled substance from unbound assay reagents and the remaining components in the test sample. The trapping substance may be immobilized on the chromatography carrier before or during the performance of the assay by means of any suitable attachment method. Further, the trapping substance may be provided in a single detection site or in multiple sites on or in the chromatography carrier. The trapping substance may also be provided in a variety of configurations to produce different detection or measurement formats. For example, the trapping substance may be configured as a letter, number, icon, or symbol, or any combination thereof.

In particular, the present invention provides a chromatography assay device for detecting the presence of an analyte in a sample, preferably a blood sample. The device is preferably in the form of a chromatographic strip having a chromatographic carrier defining a path for fluid flow and which is capable of supporting capillary flow, an application site for the blood sample, and a detection site spaced apart from the application site for detecting the presence or amount of analyte present in the blood sample. Preferably, the device also includes a labeled substance (or conjugate) diffusively bound to the chromatographic carrier. In a preferred embodiment, the labeled substance will bind to the analyte or will compete with the analyte for binding at the detection site. The device preferably contains two additional agents diffusively bound to the chromatographic carrier: (1) a red blood cell separating agent upstream (hereinafter, the direction of the movement of a sample caused by capillary action is called "downstream" and the opposite direction is called "upstream") of the detection site which is capable of separating plasma or serum from the blood sample, and (2) a neutralizing agent downstream of the red blood cell separating agent and upstream of the detection site to neutralize any effect, particularly an adverse effect, of the red blood cell separating agent on the chromatography system.

In the context of the present invention, the phrase "diffusively bound" as applied to a given reagent may be defined as any reagent used in the present invention, including but not limited to, a labeled substance, specific binding member, red blood cell separating agent or neutralizing agent, is intended to denote that the reagent(s) is/are bound in a fashion that permits the bound reagent(s) to flow along the flow path.

For purposes of the present invention, any assay system may be employed. Immunoassay systems are preferred, including but not limited to, lateral flow systems, vertical flow systems, soak systems, and dipsticks. A general description of known assay systems is set forth below.

Generally, in a chromatography strip, at least a sample application site and a detection site are arranged on a chromatography carrier. A sample solution, in this case preferably a blood sample, suspected of having an analyte of interest, i.e. an analyte, moves through the chromatography carrier by capillary action when added to the sample application site, and a labeled substance or conjugate which is contained in a labeling means arranged on a chromatography carrier in advance is accumulated at the detection site in direct or inverse proportion to the presence or quantity of the substance to be assayed in the sample solution, effected by a binding reaction (such as an immunological reaction), so that the presence or quantity of substance to be assayed in the sample solution can be found by measuring the presence or quantity of the thus accumulated labeled substance or conjugate. Various types of chromatography strips are known, and all of these known chromatography strips, including those which will be described later, can be used in the present invention. The term "chromatography assay device" as used herein means a chromatography strip which is produced in such a way that it can be used in an assay and is able to be stored and transported.

The following describes a typical example of a chromatography strip. A sample application site may be located at the same place where the labeled substance is present, preferably at a position upstream of the labeled substance. When a sample solution, suspected of containing an analyte to be assayed, is contacted with the sample application site, the sample solution moves through the chromatography carrier in the downstream direction together with the analyte effected by capillary action. Typically, the analyte is a compound which binds in a specific fashion to a trapping substance fixed to the detection site, or it is a compound which binds in a specific fashion to a conjugate that binds specifically to the trapping substance at the detection site. For example, the analyte is an antibody when the trapping substance is an antigen or the conjugate contains an antigen, and the analyte is an antigen when the trapping substance is an antibody or the conjugate contains an antibody. By way of further example, the analyte may be a nucleic acid which binds to a complementary conjugate and trapping substance.

When the sample application site is located at an upstream position to a labeled substance, the labeled substance may be arranged adjacent to the sample application site or on a position disconnected from the sample application site.

Addition of the labeled substance can be effected by various means, for example by adding it to a certain position outside the chromatography strip detection site after addition of the sample solution.

Since the labeled substance is arranged in such a manner that it moves by the capillary action of the sample solution, the labeled substance moves in the downstream direction when the sample solution is added to the sample adding means.

The detection site is generally located at a downstream position from the labeled substance and at a certain distance from the labeled substance. In the detection site, a trapping substance which binds only to an analyte or a conjugate in a specific fashion, or binds specifically to each of the substances to be assayed and a labeled substance, is fixed to the chromatography carrier. Consequently, in one embodiment the analyte (sometimes linked to a labeled substance), moved by capillary action of the sample solution, binds to the trapping substance or to a conjugate which in turn binds to the trapping substance. The labeled substance binds to the thus bound substance to be assayed, thereby effecting accumulation of the labeled substance in the detecting means in response to the presence or quantity of the analyte. Alternatively, the labeled substance and the analyte, moved by capillary action, bind competitively to the trapping substance or to a conjugate which in turn binds to the trapping substance, thereby effecting accumulation of the labeled substance in inverse proportion to the quantity of substance to be assayed.

There is a case in which a certain labeled substance binds both a trapping substance (or a conjugate which in turn binds a trapping substance) and an analyte, but not simultaneously and, in that case, the analyte firstly binds to the labeled substance and the remaining labeled substance which did not bind to the substance to be assayed binds to the trapping substance. In consequence, the presence or quantity of the analyte can be analyzed by measuring the labeled substance accumulated in the detecting means.

As occasion demands, various substances are located upstream of the detection site. For example, a conjugate may be so located in a movable manner.

In some cases, one or more additional detection sites may be arranged downstream of the first detection site. Also, downstream of the detection site there may be a further extension of the chromatography carrier so that a sample solution can be discharged completely or the carrier may be equipped with a material for use in the absorption of the sample solution.

Thus, the presence or quantity of an analyte of interest in a sample solution can be found by measuring the presence or quantity of a labeled substance accumulated in the detection site. In one instance, this may be accomplished visually.

The present invention is intended to be used with any blood sample, including serum and plasma, but is preferably used with a blood sample containing red blood cells, e.g., whole blood.

Before assaying for the analyte of interest in the blood sample, the red blood cells are preferably removed if the assay is to work with the desired sensitivity. Thus, according to the present invention, a red blood cell separating agent is bound to the chromatography carrier. Preferably, the red blood cell separating agent is diffusively bound to the chromatography carrier. The red blood cell separating agent may be bound to the chromatography carrier at any location which will function to separate the red blood cells from the plasma or serum. It is preferably diffusively bound to the chromatographic carrier upstream of the detection site. Most preferably the red blood cell separating agent is diffusively bound at the sample application site. This location is preferable because it causes aggregation of the red blood cells as soon as they are applied to the chromatography carrier resulting in minimal, if any, interference in the flow of the serum or plasma along the carrier by capillary action.

The red blood cell separating agent of the present invention may be any substance capable of aggregating red blood cells. Preferred agents are positively charged materials such as polycations, including e.g., poly-L-lysine hydrobromide; poly(dimethyl diallyl ammonium) chloride (Merquat®-100, Merquat® 280, Merquat® 550); poly-L-arginine hydrochloride; poly-L-histidine; poly(4-vinylpyridine), poly(4-vinylpyridine) hydrochloride; poly(4-vinylpyridine)cross-linked, methylchloride quaternary salt; poly(4-vinylpyridine-co-styrene); poly(4-vinylpyridinium poly (hydrogen fluoride)); poly(4-vinylpyridinium-P-toluene sulfonate); poly(4-vinylpyridinium-tribromide); poly(4-vinylpyrrolidone-co-2-dimethylaminoethyl methacrylate); poly vinylpyrrolidone, cross-linked; poly vinylpyrrolidone, poly(melamine-co-formaldehyde); partially methylated; hexadimethrine bromide; poly(Glu, Lys) 1:4 hydrobromide; poly(Lys, Ala) 3:1 hydrobromide; poly(Lys, Ala) 2:1 hydrobromide; poly-L-lysine succinylated; poly(Lys, Ala) 1:1 hydrobromide; and poly(Lys, Trp) 1:4 hydrobromide. The most preferred polycation is poly (dimethyl diallyl ammonium) chloride (Merquat®-100).

The red blood cell separating agent of the present invention may be used in any suitable amount which functions to separate the red blood cells from the rest of the sample. Preferably, the red blood cell separating agent may be present in a concentration of from about 0.04% to about 1.3% (weight per volume), with from about 0.13% to about 0.33% (weight per volume) being more preferred, and about 0.20% to about 0.33% (weight per volume) being most preferred.

A positive charge on the red blood cell separating agent has a tendency to aggregate any negatively charged agent present on the strip. For example, a labeled substance or conjugate bound to the chromatography carrier may also be aggregated by the red blood cell separating agent interfering with binding of the analyte to the conjugate or, in a competitive assay, the binding of the labeled substance and the analyte of interest to the trapping substance at the detection site or a conjugate. Ultimately, the sensitivity and accuracy of the immunoassay system may be compromised.

Accordingly, when the blood cell separating agent is a positively charged material, the present invention preferably employs a neutralization agent. The neutralization agent is capable of neutralizing the positive charge of the red blood cell separating agent, thereby eliminating or at least minimizing any interference to the assay system caused by the red blood cell separating agent. Preferably, the neutralization agent is diffusively bound to the chromatographic carrier. The neutralizing agent may be diffusively bound at any location on the chromatographic carrier where it will function to neutralize a red blood cell separating agent, but is preferably located downstream of the red blood cell separating agent and upstream of the detection site, and more preferably is located at the same place on the chromatography as the diffusively bound labeled substance.

The neutralizing agent may be any polyanion capable of neutralizing the positive charge of the red blood cell separating agent. Preferred polyanions include poly(acrylic acid), poly(acrylic acid, Na salt), poly(methyl methacrylic acid), poly(Na-4-styrene sulfonate), poly(vinyl sulfonic acid), poly-L-aspartic acid, and carboxymethyl cellulose, with dextran sulfate being the most preferred.

The neutralization agent may be present in any amount which functions to neutralize the positive charge of the red blood cell separating agent. Generally, the concentration of the neutralization agent is dependent upon the concentration of the red blood cell separating agent being used. Preferably, the neutralizing agent is present in a concentration of from about 0.33% to about 20% (weight per volume), with about 0.34% to about 10% (weight per volume) being more preferred and 0.34% to 10% (weight per volume) being most preferred.

FIG. 1 depicts an embodiment of an immunochromatography assay device according to the present invention. The device 10 comprises a chromatography carrier 20. Located on the chromatography carrier 20 is an application site 30 for the blood sample. In this preferred embodiment, the red blood cell separating agent, i.e., Merquat®100, is located on the application site 30. Adjacent to the application site 30 is a conjugate pad 40 containing the conjugate, i.e. selenium labeled binding substance and a neutralizing agent, i.e., dextran sulfate. Further downstream is the detection site 50 which after the assay has been run will exhibit a control bar 60 and if the substance to be assayed is present, a test bar 70.

In another embodiment of the present invention, a buffer may be contacted with the application site, preferably after the application site has been contacted with the sample. The buffer aids in maintaining an acceptable fluid flow rate along the flow path on the chromatographic carrier. The buffer may be any substance which is capable of flowing by capillary action along the fluid flow path including, but not limited to, phosphate buffer, phosphate buffer saline, Tris—HCl buffer, carbonate buffer, citrate buffer, HEPES (2-hydroxypiperazine-N'-2-ethanesulfonic acid) buffer, MOPS (3-(N-morpholino)propanesulfonic acid) buffer, MES (2-(N-morpholino)ethanesulfonic acid) buffer, and the like. Although the concentration and pH may be any concentration and pH which will work in the desired assay device, preferably the molarity is an a range of from about 10 mM to about 100 mM and the pH is from about 5–9 and more preferably from about 6–8. Most preferably, the buffer employed is 50 mM phosphate buffer, pH 7.4.

The fluid volume employed in the present invention is dependent upon the device size. Desirably, enough fluid volume is used to permit fluid flow through the device to the detection site. Preferably, the fluid volume is in a range of about 25 $\mu$l to about 100 $\mu$l, and more preferably from about 40 $\mu$l to about 60 $\mu$l. Accordingly, the buffer, when needed, may be added in a volume range of from about 10 $\mu$l to about 40 $\mu$l, and more preferably from about 20 $\mu$l to about 30 $\mu$l.

The present invention is also directed to a method for detecting the presence of an analyte in a blood sample. Preferably, the method employs the chromatography immunoassay device of the present invention. Specifically, the method comprises (1) providing a chromatography carrier which defines a path for fluid flow capable of supporting capillary flow, along which are an application site for the blood sample which is in fluid contact with the chromatography carrier, a detection site on the chromatography carrier spaced apart from the application site, a diffusively labeled substance (or a conjugate) which binds to or competes with the analyte for binding at the detection site, a diffusively bound red blood cell separating agent for separating plasma or serum from said blood sample upstream of the detection site, and a conjugate bound to the chromatography carrier; (2) contacting the application site with the blood sample such that the red blood cell separating agent separates the red blood cells from the plasma or serum of the blood sample, and the neutralizing agent neutralizes the positive charge of the separating agent; and (3) detecting the presence of analyte in the blood sample.

Preferably, the blood cell separating agent is a positively charged material and the path of fluid flow contains a diffusively bound neutralizing agent, which is preferably capable of binding with said red blood cell separating agent and is located downstream of said red blood cell separating agent and upstream of said detection site whereby the positive charge of said separating agent is neutralized.

Thus, in the preferred embodiment of FIG. 1, a blood sample is applied to the application site 30 and the red blood cell separating agent separates the red blood cells by aggregating them and permitting the plasma or serum to move by capillary action down the chromatographic carrier 20. The neutralizing agent in the conjugate pad 40 neutralizes the effects of the red blood cell separating agent on the device 10 and conjugate and the analyte binds to the conjugate present in the conjugate pad 40. The analyte bound to the conjugate continues to move downstream to the detection site 50. If the analyte of interest is present the test bar 70 will appear. To indicate that the test is working properly, the control bar 60 will appear whether the analyte of interest is present or not.

The present invention may preferably include a non-reactive cover or enclosure around the device. Preferably, the cover encloses at least the chromatography carrier to avoid contact with and contamination of the capture sites. The cover may also include a raised area adjacent to the application site to facilitate receiving and/or containing a certain volume of the sample. Additionally, the cover may include a cut out area or areas in the form of a letter, number, icon, or symbol, or any combination thereof. In this embodiment, the cut out area or areas form the design for particular detection site(s) when the strip is completely closed. It is preferred that a sufficient portion of the strip be encased to prevent applied sample from contacting the detection sites without first passing through a portion of the strip.

The device and method of the present invention may be used in any assay system in which a blood sample contains an analyte of interest. Examples of preferred systems include, but are not limited to, Hepatitis C virus ("HCV"), hepatitis A virus ("HAV"), Human Immunodeficiency Virus ("HIV"), hepatitis B surface antibody ("HBsAb"), hepatitis B surface antigen ("HBsAg"), hepatitis B core antibody ("HBcAb"), hepatitis B core antigen ("HBcAg"), Carcinoembryonic antigen ("CEA"), alpha-fetoproten ("AFP"), a pancreatic cancer marker ("CA19–9"), syphilis, tuberculosis, malaria, Leishmania, and Dengue fever.

The following examples further illustrate the present invention, but should not be construed, in any way, as limiting its scope.

EXAMPLES

Example 1

Red Blood Cell Aggregation vs. Se-Conjugate Aggregation by Polycations

For the purpose of the present invention, aggregation of red blood cells (rbc's) in whole blood is desired while aggregation of the selenium conjugate is not wanted. Various polycations were tested to see which would cause sufficient aggregation of rbc's while only minimally aggregating the selenium conjugate.

Selenium conjugate of HIV-1 recombinant protein was prepared in the following manner: First, selenium colloid was prepared by reacting 32 mM selenium oxide with 91 mM L-ascorbic acid in an aqueous solution for 72 hours at 42° C. This selenium colloid was diluted to an optical density of 30 at a wavelength of 550 nm and then reacted with 40 µg/ml of recombinant HIV-1 envelope protein in 30 mM Tris buffer, pH 7.4 for 20 minutes at room temperature. This selenium colloid-labeled HIV-1 protein conjugate was next diluted to an optical density of 30 at a wavelength of 550 nm in 10 mM Tris buffer, pH 7.4 containing 0.1% casein, and incubated for 20 minutes at room temperature. The conjugate solution was then centrifuged at 1970×g for 20 minutes at 4° C., the supernatant removed and the pellet discarded. A volume of 30 mM Tris buffer, pH 7.4 containing 2% casein, equivalent to one-tenth the volume of the supernatant, was then added to the supernatant. Finally, this conjugate solution was diluted to an optical density of 10 at a wavelength of 550 nm in 50 mM Tris buffer, pH 7.4 containing 1% casein, 2% sucrose and 2% lactose.

Aqueous solutions of the following polycations were prepared at 0.25% (w/v): Poly-L-Lysine hydrobromide, molecular weight (mw) 37000; Poly-L-Arginine hydrochloride, mw 12100, 42400 and 92000; Poly-L-Histidine, mw 18400;

Hexadimethrine bromide, Poly (Lysine, Alanine) 3:1 hydrobromide, mw 35000; Poly (Lysine, Alanine) 2:1 hydrobromide, mw 49300; Poly (Lysine, Alanine) 1:1 hydrobromide, mw 41600, Poly (Lysine, Tryptophan) 1:4 hydrobromide, mw 38000 (All of the above polycations were purchased from Sigma, St. Louis, Mo.);

Poly(diallyldimethylammonium chloride), mw $10^5$ to $10^6$ (Merquat®-100, Calgon, Pittsburgh, Pa.).

The ability of these polycations to aggregate either rbc's in whole blood or the selenium conjugate were observed in separate reactions by adding 350 µl of 0.25% of the various polycation solutions to an equal volume of either whole blood or the selenium conjugate. The solutions were mixed and stored at room temperature for 10 minutes, then aggregation was evaluated visually. The results are summarized in Table 1. A one-plus (+) indicates weak aggregation, 2+ indicates moderate aggregation, and 3+ and 4+ indicate strong aggregation.

TABLE 1

| Polycation | Molecular Weight | Aggregation | |
|---|---|---|---|
| | | Red Blood Cells | Se-Conjugate |
| Poly-L-Lys HBr | 37000 | 2+ | 2+ |
| Merquat ®-100 | $10^5$ to $10^6$ | 2+ | 2+ |
| Poly-L-Arg HCl | 12100 | 2+ | 2+ |
| Poly-L-Arg HCl | 42400 | 2+ | 2+ |
| Poly-L-Arg HCl | 92000 | 2+ | 2+ |
| Poly-L-His | 18400 | + | 4+ |
| Hexadimethrine Br | | + | + |
| Poly (Lys, Ala) 3:1 HBr | 35000 | 2+ | 2+ |
| Poly (Lys, Ala) 2:1 HBr | 49300 | + | 2+ |
| Poly (Lys, Ala) 1:1 HBr | 41600 | + | 2+ |
| Poly (Lys, Trp) 1:4 HBr | 38000 | 3+ | 3+ |

A polycation that causes aggregation of rbc's (2+ or greater) while causing minimal aggregation of selenium conjugate (2+ or less) would be a good choice. Those polycations with a 2+ in both categories fit this criteria. Poly-L-Lysine HBr and Merquat®-100 were chosen for further work, with Merquat®-100 being the most cost effective.

Example 2

Preventing Conjugate Aggregation with Polyanion Neutralization

A. Conjugate Flow and Aggregation Prevention using Dextran Sulfate Using Poly-L-Lysine as the polycation rbc aggregating reagent, various concentrations of the polyanion dextran sulfate were tested to see if the positive charge of the polycation could be neutralized by the dextran sulfate, thus preventing aggregation of the selenium conjugate caused by the polycation. The dextran sulfate was added after the polycation had already caused aggregation of the rbc's to occur, but prior to the polycation interaction with the selenium conjugate. The following experiment evaluated the effect of the polycation and dextran sulfate on the aggregation of the selenium conjugate and its subsequent ability to flow along the immunochromatography strip.

An immunochromatography strip, composed of a Sample Pad, a Neutralization Pad, a Conjugate Pad, and a Detection Strip, was assembled. The Sample Pad was prepared by soaking a 4 mm wide by 20 mm long glass fiber filter (Lypore 9524, Lydall, Rochester, N.H.) in an aqueous solution of 0.33% Poly-L-Lysine hydrobromide, mw 37000 (Sigma, St. Louis, Mo.), then drying it under vacuum.

Neutralization Pads, containing different concentrations of Dextran Sulfate, were prepared by soaking 4 mm wide by 13 mm long filters made of wood pulp and polyester (Sontara 8801, Du pont, Wilmington, Del.) in aqueous solutions containing 0%, 1.1%, 3.3% or 10% Dextran Sulfate, mw 5000 (Sigma, St. Louis, Mo.). After soaking, the pads were dried under vacuum.

The Conjugate Pad was prepared by soaking a 4 mm wide by 4.3 mm long glass fiber filter (Lypore 9524, Lydall, Rochester, N.H.) in selenium colloid-labeled HIV-1 recombinant protein conjugate prepared and diluted as in Example 1. After soaking, the Conjugate Pad was dried under vacuum.

The Detection Strip was a 4 mm wide by 40 mm long nitrocellulose membrane filter (catalogue #H9643G1, Millipore, Bedford, Mass.). HIV-1 envelope antigen at a concentration of 5 mg/ml in 100 mM Tris buffer, pH 7.4 containing 1% sucrose was added to the nitrocellulose membrane so as to form a line across the width of the strip at a position about 1 cm from the end of the membrane. The lined region was backed with Polyester Laminate (code #7733, Adhesives Research Inc., Glen Rock, Pa.). This was allowed to dry sufficiently so as to fix the antigen to the nitrocellulose.

Immunochromatography strips, 4 mm wide, were assembled using the components above by placing them end-to-end longitudinally with a 1 mm overlap between each section, with the 20 mm long Sample Pad at one end, next to which was placed one of the 13 mm long Neutralization Pads, followed by a 4.3 mm long Conjugate Pad, and finally a 40 mm long Detection Strip. The assembled strip was then covered with Polyester Laminate (code #8648, Adhesives Research Inc., Glen Rock, Pa.) from the top of the Detection Strip to 10 mm from the bottom of the strip, leaving approximately 10 mm of the Sample Pad exposed. Eighty $\mu l$ of plasma was then applied to the Sample Pads of each of the immunochromatography strips containing Neutralization Pads with either 0%, 1.1%, 3.3% or 10% Dextran Sulfate. Aggregation of the red selenium conjugate and the ability of the conjugate to flow along the strip were observed visually.

Results, shown in Table 2 below, indicated that, without the presence of Dextran Sulfate to neutralize the charge from the polycation solution, the selenium conjugate aggregated and was not able to flow along the strip. There was an inverse relationship between conjugate aggregation and flow, with concentrations of Dextran Sulfate of 3.3% or greater being sufficient to prevent conjugate aggregation and allow conjugate to flow along the strip.

TABLE 2

| Dextran Sulfate Concentration | Conjugate Aggregation | Conjugate Flow |
|---|---|---|
| 0% | + + | − |
| 1.1% | + | +/− |
| 3.3% | − | + |
| 10% | − | + |

B. RBC Aggregation in the Presence of Dextran Sulfate In order to assess the affect of dextran sulfate on rbc aggregation, the above experiment was repeated using whole blood as the sample with 10% Dextran Sulfate on a 4.3 mm long by 4 mm wide Neutralization Pad. After assembling the immunochromatography strip as above, using this Neutralization Pad, 80 $\mu l$ of whole blood was applied to the Sample Pad. Fifteen minutes later, the result of rbc aggregation was observed visually and the ability of the resultant plasma to flow along the strip was measured. The rbc's aggregated, being retained on the Sample Pad, and did not flow onto the strip, while the plasma flowed 33 mm along the strip in 15 minutes. This indicated that the polycation in the Sample Pad was still able to cause aggregation of the rbc's in the whole blood sample, and that the presence of the polyanion, Dextran Sulfate, in the Neutralization Pad did not interfere with this rbc aggregation.

C. Conjugate Aggregation Prevention by Polyanions

Other polyanions were tested to evaluate their ability to prevent aggregation of the selenium conjugate as in Example 2.A. A 15.5 mm long by 4 mm wide Sample Pad was soaked in an aqueous solution containing 0.26% Merquat®-100, then dried at 55° C. Neutralization Pads were not used, and instead the selenium conjugate was diluted in 10 mM Tris buffer, pH 7.4 containing 1% casein, 2% sucrose, 2% lactose and 0%, 1.1% or 3.3% of the polyanion Dextran Sulfate, mw 5000 (Sigma, St. Louis, Mo.), or 0%, 0.5%, 1% or 2% of one of the following polyanions (all from Aldrich Chemical Co., Milwaukee, Wis.): Poly (acrylic acid), mw 5000; Poly (sodium-4-styrene sulfonate), mw 70,000; Poly (vinyl sulfonic acid, sodium salt); Poly (methyl methacrylic acid), mw 9500; Poly (acrylic acid, sodium salt), mw 2100. Conjugate Pads were soaked in the various selenium conjugate solutions and dried under vacuum. The Detection Strip was prepared as in Example 2.A. and immunochromatography strips were assembled. Fifty $\mu l$ of plasma was then applied to the Sample Pads of each of the immunochromatography strips containing Conjugate Pads with the various polyanions. Aggregation of the red selenium conjugate was observed visually. Table 3 shows the relative amount of conjugate aggregation seen with the various concentrations of polyanions tested.

TABLE 3

| | Selenium Conjugate Aggregation | | | | |
|---|---|---|---|---|---|
| | Polyanion Concentration | | | | |
| Polyanion | 0% | 0.5% | 1–1.1% | 2% | 3.3% |
| Dextran Sulfate | + + | nt | + | nt | − |
| Poly (acrylic acid) | + + | − | − | − | nt |
| Poly (Na-4-styrene sulfonate) | + + | + + | + + | + | nt |
| Poly (vinyl sulfonic acid) | + + | +/− | − | − | nt |

TABLE 3-continued

Selenium Conjugate Aggregation

| | Polyanion Concentration | | | | |
|---|---|---|---|---|---|
| Polyanion | 0% | 0.5% | 1–1.1% | 2% | 3.3% |
| Poly (methyl methacrylic acid) | + + | – | – | – | nt |
| Poly (acrylic acid, Na salt) | + + | + | +/– | – | nt | nt = not tested

As before, the selenium conjugate aggregated if there was not a polyanion present to neutralize the positive charge of the polycation from the Sample Pad (which is necessary for rbc aggregation when testing whole blood). All of the polyanions used in the Conjugation Pad prevented conjugate aggregation from occurring at at least one of the concentrations tested. This experiment also showed that the polyanion did not have to be applied to a separate pad, but could be combined with the selenium conjugate on the Conjugation Pad.

Example 3

Use of Dextran Sulfate in Neutralization Pad vs. Conjugation Pad in an HIV-1 Antibody Assay Immunochromatography strips were prepared as in Example 2.A. either with or without a 4 mm wide by 4.3 mm long glass fiber filter (Lypore 9524, Lydall, Rochester, N.H.) Neutralization Pad. When used, the Neutralization Pad was soaked in an aqueous solution containing 3.3% Dextran Sulfate, then dried under vacuum. In strips without a Neutralization Pad, the selenium conjugate was diluted in 10 mM Tris buffer, pH 7.4 containing 1% casein, 2% sucrose, 2% lactose and 3.3% Dextran Sulfate, and the Conjugate Pad was soaked in this solution then dried under vacuum. The Sample Pad used was as in Example 2.A. except that it was soaked in an aqueous solution of 0.2% Merquat®-100.

Human serum containing HIV-1 antibodies was diluted 1:2048 into either HIV negative human whole blood (based on plasma volume) with a hematocrit value of 50% or into HIV negative human plasma. Three further 1:2 serial dilutions were made, again using either whole blood or plasma as the diluent. Eighty µl of negative whole blood or samples from the HIV-1 positive whole blood dilution series were added to the Sample Pad of immunochromatography strips prepared with Dextran Sulfate on a separate Neutralization Pad or Dextran Sulfate in the selenium conjugate solution on the Conjugate Pad. Eighty µl of negative plasma or samples from the HIV-1 positive plasma dilution series were tested only on immunochromatography strips with Dextran Sulfate on the Conjugate Pad. Results were read 15 minutes after sample application (Table 4). A positive result showed a red color on the Detection Strip where the red selenium HIV-1 antigen conjugate-HIV-1 antibody complex was bound to the HIV-1 antigen on the lined region of the strip. A negative result showed no color at this region on the Detection Strip.

TABLE 4

| Sample Dilution | Dextran Sulfate in Neutralization Pad | Dextran Sulfate in Conjugate Pad | |
|---|---|---|---|
| | Whole Blood | Whole Blood | Plasma |
| 1:2048 | + | + | + |
| 1:4096 | + | + | + |
| 1:8192 | – | + | + |
| 1:16384 | nt | – | – |
| Negative Control | – | – | – | nt = not tested

The results in Table 4 indicate that HIV-1 antibodies are detectable from whole blood in an immunochromatography strip assay using the polycation Merquat®-100 to aggregate rbc's and allow sample to flow along the strip, and the polyanion Dextran Sulfate as a neutralizing agent, preventing aggregation of the selenium conjugate by the polycation and allowing the conjugate to bind and form a complex with a positive sample and flow along the strip to the detection area. The polyanion was shown to be effective when used either in a separate Neutralization Pad or combined with the selenium conjugate on the Conjugate Pad. In this assay, the sensitivity for detecting HIV-1 antibodies showed a 2-fold improvement when the polyanion (Dextran Sulfate) was used in the Conjugate Pad rather than on a separate Neutralization Pad.

Additionally, the results in Table 4 indicate that the polycation is effectively aggregating the rbc's in the whole blood as shown by the equal sensitivity of detection of HIV-1 antibodies whether in whole blood, where the rbc's must be aggregated for the sample to flow, or plasma, where there are no rbc's to prevent sample flow. This also shows that the presence of the polyanion, in either a separate Neutralization Pad or in the Conjugate Pad, does not interfere with the ability of the polycation to effectively cause aggregation of rbc's in whole blood.

Example 4

Use of Merquat® and Various Polyanions in an HBsAg Assay

Immunochromatography strips were prepared for the detection of Hepatitis B surface antigen (HBsAg) in whole blood samples. Merquat®-100 was used as the polycation for the aggregation of rbc's in the Sample Pad, and various polyanions were evaluated in the Conjugate Pad as polycation neutralization reagents to prevent aggregation of the selenium conjugate.

Immunochromatography strips, composed of a Sample Pad, a Conjugate Pad, and a Detection Strip, were assembled. The Sample Pad was prepared by soaking a 4 mm wide by 15.5 mm long glass fiber filter in an aqueous solution of 0.26% Merquat®-100, then drying it at 55° C.

The selenium conjugate was prepared using selenium colloid, as in Example 1, and 12 µg/ml mouse monoclonal antibody to HBsAg (anti-HBs). This selenium colloid-labeled anti-HBs conjugate was then diluted to an optical density of 2.6 at a wavelength of 550 nm in Tris buffer containing one of the following polyanions: 0.5% Poly (acrylic acid), mw 2000 (PAA-2000); 0.5% Poly (acrylic acid), mw 240,000 (PAA-240,000); 0.5% Dextran Sulfate, mw 5000; 0.8% Poly-L-aspartic acid, mw 36,300; 0.5% Carboxymethyl cellulose, mw 90,000 (CMC). The Dextran Sulfate and Poly-L-aspartic acid were from Sigma, St.

Louis, Mo., and the remaining polyanions were from Aldrich Chemical Co., Milwaukee, Wis.

The Conjugate Pad was prepared by soaking a 4 mm wide by 4.3 mm long glass fiber filter in selenium colloid-labeled anti-HBs conjugate prepared and diluted with one of the polyanions above. After soaking, the Conjugate Pad was dried under vacuum.

The Detection Strip was a 4 mm wide by 40 mm long nitrocellulose membrane filter, prepared as in Example 2 using mouse monoclonal anti-HBs at a concentration of 3 mg/ml and added to the nitrocellulose membrane so as to form a line across the width of the strip at a position about 1 cm from the end of the membrane. The lined region was backed with Polyester Laminate. This was allowed to dry sufficiently so as to fix the antibody to the nitrocellulose.

Immunochromatography strips were assembled using the components above by placing them end-to-end longitudinally, with a 1 mm overlap, with the Sample Pad at one end, next to which was placed a Conjugate Pad, and finally a Detection Strip. The assembled strip was then covered with Polyester Laminate, leaving approximately 10 mm of the Sample Pad exposed.

Recombinant HBsAg was added to HBsAg negative human whole blood with a hematocrit value of 50% to a concentration of 12.5 mg/ml. Three further 1:2 serial dilutions were made in whole blood. Fifty µl of negative whole blood or samples from the HBsAg positive whole blood dilution series were added to the Sample Pad of immunochromatography strips prepared with various polyanions in the Conjugate Pad. Results were read 15 minutes after sample application (Table 5). A positive result showed a red color on the Detection Strip where the red selenium anti-HBs conjugate-HBsAg complex was bound to the anti-HBs on the lined region of the strip. A negative result showed no color at this region on the Detection Strip. Aggregation of the red selenium conjugate at the entrance to the Detection Strip was observed visually.

TABLE 5

| Polyanion | Concentration of HBsAg ng/ml | | | | | Conjugate Aggregation |
|---|---|---|---|---|---|---|
| | 12.5 | 6.25 | 3.13 | 1.56 | 0 | |
| PAA-2000 | + | + | + | − | − | − |
| PAA-240,000 | + | + | − | − | − | + |
| Dextran Sulfate | + | + | + | − | − | − |
| Poly-L-Asp | + | + | + | − | − | − |
| CMC | + | − | − | − | − | + |

While all polyanions allowed HBsAg detection to occur, those polyanions that prevented conjugate aggregation, PAA-2000, Dextran Sulfate and Poly-L-aspartic acid, exhibited a 2 to 4-fold more sensitive detection of HBsAg in whole blood samples.

The above experiment was repeated, using the selenium colloid-labeled conjugate diluted in Tris buffer containing PAA-2000 as the polyanion, except 25 µl of 50 mM phosphate buffer, pH 7.4, was added to the sample pad one minute after addition of the HBsAg whole blood samples. The results obtained using this procedure, with the addition of the buffer after the sample application, were identical to the results without this step. Thus, these assays can be done either with or without addition of buffer after sample application.

Example 5

Use of Merquat® and Dextran Sulfate in an Assay for Tuberculosis

Immunochromatography strips were prepared for the detection of antibody to *Mycobacterium tuberculosis* (anti-Mtb) in whole blood samples. Merquat®-100 was used as the polycation for the aggregation of rbc's in the Sample Pad, and various concentrations of the polyanion Dextran Sulfate were evaluated in the Conjugate Pad as the polycation neutralization reagent to prevent aggregation of the selenium conjugate.

Immunochromatography strips, composed of a Sample Pad, a Conjugate Pad, and a Detection Strip, were assembled. The Sample Pad was prepared by soaking a 4 mm wide by 15.5 mm long glass fiber filter in an aqueous solution of 0.26% Merquat®-100, then drying it in a vacuum.

The selenium conjugate was prepared using selenium colloid, as in Example 1, and 3.5 µg/ml of recombinant Mtb antigen from *E. coli*. This selenium colloid-labeled Mtb conjugate was then diluted to an optical density of 2.5 at a wavelength of 550 nm in Tris buffer containing either 0%, 0.34%, 1.1% or 3.3% Dextran Sulfate.

The Conjugate Pad was prepared by soaking a 4 mm wide by 4.3 mm long glass fiber filter in selenium colloid-labeled Mtb conjugate, prepared and diluted with one of the Dextran Sulfate concentrations above. After soaking, the Conjugate Pad was dried under vacuum.

The Detection Strip was a 4 mm wide by 40 mm long nitrocellulose membrane filter, prepared as in Example 2 using recombinant Mtb antigen at a concentration of 0.15 mg/ml and added to the nitrocellulose membrane so as to form a line across the width of the strip at a position about 1 cm from the end of the membrane. The lined region was backed with Polyester Laminate. This was allowed to dry sufficiently so as to fix the antigen to the nitrocellulose.

Immunochromatography strips were assembled using the components above by placing them end-to-end longitudinally, with a 1 mm overlap, with the Sample Pad at one end, next to which was placed a Conjugate Pad, and finally a Detection Strip. The assembled strip was then covered with Polyester Laminate, leaving approximately 10 mm of the Sample Pad exposed.

Anti-Mtb positive serum was diluted 1:100 into negative human whole blood with a hematocrit value of 50%. Two further 1:2 serial dilutions were made in whole blood. Fifty µl of negative whole blood or samples from the anti-Mtb positive whole blood dilution series were added to the Sample Pad of immunochromatography strips prepared with various concentrations of Dextran Sulfate in the Conjugate Pad. Results were read 15 minutes after sample application (Table 6). A positive result showed a red color on the Detection Strip where the red selenium Mtb conjugate-anti-Mtb complex was bound to the Mtb on the lined region of the strip. A negative result showed no color at this region on the Detection Strip. Aggregation of the red selenium conjugate at the entrance to the Detection Strip was observed visually.

TABLE 6

| Dextran Sulfate (%) | Anti-Mtb Dilution | | | Neg. Control | Conjugate Aggregation |
|---|---|---|---|---|---|
| | 1:100 | 1:200 | 1:400 | | |
| 0 | − | − | − | − | + + |
| 0.34 | − | − | − | − | + + |
| 1.1 | + | − | − | − | + |
| 3.3 | + | + | − | − | − |

The data in Table 6 shows that the assay does not work without the presence of a polyanion, in this case Dextran Sulfate, to prevent aggregation of the conjugate. There is an inverse relationship between conjugate aggregation and assay sensitivity. At a Dextran Sulfate concentration of 3.3%, no conjugate aggregation occurs and the assay shows the most sensitive detection of anti-Mtb.

Example 6
Syphilis Assay using Merquat® and Dextran Sulfate

Immunochromatography strips were prepared for the detection of antibody to *Treponema pallidum* (anti-TP) in whole blood or plasma samples. By comparing sensitivity of detection in whole blood to plasma, one could determine whether rbc's in whole blood were effectively being aggregated by the polycation so as not to interfere with and thereby decrease the sensitivity of detection of the assay. Merquat®-100 was used as the polycation for the aggregation of rbc's in the Sample Pad, and the poly-anion Dextran Sulfate was used in the Conjugate Pad as the polycation neutralization reagent to prevent aggregation of the selenium conjugate.

Immunochromatography strips, composed of a Sample Pad, a Conjugate Pad, and a Detection Strip, were assembled. The Sample Pad was prepared by soaking a 4 mm wide by 15.5 mm long glass fiber filter in an aqueous solution of 0.2% Merquat®-100, then drying it at 55° C.

The selenium conjugate was prepared using selenium colloid, as in Example 1, and 7.5 µg/ml of Treponema pallidum lysate (TP). This selenium colloid-labeled TP conjugate was then diluted to an optical density of 2.8 at a wavelength of 550 nm in Tris buffer containing 3.3% Dextran Sulfate.

The Conjugate Pad was prepared by soaking a 4 mm wide by 4.3 mm long glass fiber filter in the selenium colloid-labeled TP conjugate prepared above. After soaking, the Conjugate Pad was dried under vacuum.

The Detection Strip was a 4 mm wide by 40 mm long nitrocellulose membrane filter, prepared as in Example 2 using *Treponema pallidum* lysate at a concentration of 44 µg/ml and added to the nitrocellulose membrane so as to form a line across the width of the strip at a position about 1 cm from the end of the membrane. The lined region was backed with Polyester Laminate. This was allowed to dry sufficiently so as to fix the TP lysate to the nitrocellulose.

Immunochromatography strips were assembled using the components above by placing them end-to-end longitudinally, with a 1 mm overlap, with the Sample Pad at one end, next to which was placed a Conjugate Pad, and finally a Detection Strip. The assembled strip was then covered with Polyester Laminate, leaving approximately 10 mm of the Sample Pad exposed.

Anti-TP positive human serum was diluted 1:10.8 into either negative human whole blood with a hematocrit value of 50% or into negative human plasma. Four further 1:2 serial dilutions were made, again using either whole blood or plasma as the diluent. Sixty µl of negative whole blood or plasma, or samples from the anti-TP positive whole blood or plasma dilution series were added to the Sample Pad of the immunochromatography strips. Results were read 15 minutes after sample application (Table 7). A positive result showed a red color on the Detection Strip where the red selenium TP conjugate-anti-TP complex was bound to the TP lysate on the lined region of the strip. A negative result showed no color at this region on the Detection Strip.

Table 7 shows that the sensitivity for detection of anti-TP was the same in both whole blood and plasma, indicating the polycation, Merquat®-100, effectively aggregated the rbc's in the whole blood.

TABLE 7

| Anti-TP Sample Dilution | Whole Blood | Plasma |
|---|---|---|
| 1:10.8 | + | + |
| 1:21.6 | + | + |
| 1:43.2 | + | + |
| 1:86.4 | + | + |
| 1:172.8 | − | − |
| Negative Control | − | − |

All publications, patents, and patent applications cited herein are hereby incorporated by reference to the same extent as if each individual document were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention be practiced otherwise than as specifically described herein. Accordingly, this invention includes all modifications encompassed within spirit and scope of the invention as set forth in the specification and accompanying claims.

What is claimed is:

1. A chromatography assay device for detecting the presence of an analyte in a blood sample comprising:
   a chromatography carrier which defines a path for fluid flow and supports capillary flow,
   an application site for said blood sample in fluid flow contact with said chromatography carrier,
   a detection site on said chromatography carrier spaced apart from said application site having a non-diffusively bound trapping substance bound thereto,
   a diffusively bound labeled substance located downstream of said application site,
   a diffusively bound polycation for separating plasma or serum from said blood sample upstream of said detection site, and
   a diffusively bound polyanion for neutralizing the polycation downstream of said bound polycation and upstream of said detection site.

2. The chromatography assay device of claim 1, wherein said device is an immunoassay device.

3. The chromatography assay device of claim 1, wherein said polycation is bound at said site for application of said blood sample.

4. The chromatography assay device of claim 1, wherein said polycation is selected from the group consisting of poly-L-lysine hydrobromide, poly-L-arginine hydrochloride, poly-L-histidine, poly (lysine, alanine) 3:1 hydrobromide, poly (lysine, alanine) 2:1 hydrobromide, poly (lysine, alanine) 1:1 hydrobromide, poly (lysine, tryptophan) 1:4 hydrobromide, and poly (diallyldimethylammonium chloride).

5. The chromatography assay device of claim 1, wherein said polycation is poly (diallyldimethylammonium chloride).

6. The chromatography assay device of claim 1, wherein said polyanion is selected from dextran sulfate, poly (acrylic acid), poly (sodium-4-styrene sulfonate), poly (vinyl sulfonic acid), poly (methyl methacrylic acid), poly-L-aspartic acid and carboxymethyl cellulose.

7. The chromatography assay device of claim 1, wherein said polyanion is dextran sulfate.

8. The chromatography assay device of claim 1, wherein said polyanion is diffusively bound to the chromatography carrier at the same location as said labeled substance.

9. The chromatography assay device of claim 1, wherein said labeled substance is a selenium labeled substance.

10. A method for detecting the presence of an analyte in a blood sample comprising the steps of:
    providing a chromatography carrier which defines a path for fluid flow and supports capillary flow, along which are (a) an application site for said blood sample in fluid flow contact with said chromatography carrier, (b) a detection site on said chromatography carrier spaced apart from said application site having a non-diffusively bound trapping substance bound thereto, (c) a labeled substance located downstream of said application site, (d) a diffusively bound polycation for separating plasma or serum from said blood sample upstream of said detection site, and (e) a diffusively bound polyanion for neutralizing the polycation located downstream of said bound polycation and upstream of said detection site;
    contacting said application site with said blood sample; and
    detecting the presence of an analyte in said blood sample.

11. The method of claim 10, wherein said labeled substance comprises a selenium labeled substance.

12. The method of claim 10, wherein said polyanion is diffusively bound to the chromatography carrier at the same location as said labeled substance.

13. The method of claim 10, wherein said polycation is selected from the group consisting of poly-L-lysine hydrobromide, poly-L-arginine hydrochloride, poly-L-histidine, poly (lysine, alanine) 3:1 hydr5obromide, poly (lysine, alanine) 2:1 hydrobromide, poly (lysine, alanine) 1:1 hydrobromide, poly (lysine, tryptophan) 1:4 hydrobromide, and poly (diallyldimethylammonium chloride).

14. The method of claim 10, wherein said polyanion is selected from dextran sulfate, poly (acrylic acid), poly (sodium-4-styrene sulfonate), poly (vinyl sulfonic acid), poly (methyl methacrylic acid), poly-L-aspartic acid and carboxymethyl cellulose.

15. A method for detecting the presence of Human Immunodeficiency Virus type 1 or Human Immunodeficiency Virus type 2 in a blood sample comprising:
    providing a chromatography carrier which defines a path for fluid flow and supports capillary flow, along which are (a)an application site for said blood sample in fluid flow contact with said chromatography carrier,
    (b)a detection site on said chromatography carrier spaced apart from said application site having a non-diffusively bound trapping substance bound thereto,
    (c)a labeled substance located downstream of said application site,
    (d)a diffusively bound polycation for separating plasma or serum from said blood sample upstream of said detection site, and
    (e)a diffusively bound polyanion for neutralizing the polycation downstream of said bound polycation and upstream of said detection site;
    contacting said application site with said blood sample; and
    detecting the presence of the Human Immunodeficiency Virus type 1 or Human Immunodeficiency Virus type 2 in said blood sample.

16. A method for detecting the presence of Hepatitis B surface antigen in a blood sample comprising:
    providing a chromatography carrier which defines a path for fluid flow and supports capillary flow, along which are
    (a)an application site for said blood sample in fluid flow contact with said chromatography carrier,
    (b)a detection site on said chromatography carrier spaced apart from said application site having a non-diffusively bound trapping substance bound thereto,
    (c) a labeled substance located downstream of said application site,
    (d)a diffusively bound polycation for separating plasma or serum from said blood sample upstream of said detection site, and
    (e)a diffusively bound polyanion for neutralizing the polycation downstream of said bound polycation and upstream of said detection site;
    contacting said application site with said blood sample; and
    detecting the presence of the Hepatitis B Surface antigen in said blood sample.

17. A method for detecting the presence of *Treponema pallidum* in a blood sample comprising:
    providing a chromatography carrier which defines a path for fluid flow and supports capillary flow, along which are
    (a)an application site for said blood sample in fluid flow contact with said chromatography carrier,
    (b)a detection site on said chromatography carrier spaced apart from said application site having a non-diffusively bound trapping substance bound thereto,
    (c)a labeled substance located downstream of said site,
    (d)a diffusively bound polycation for separating plasma or serum from said blood sample upstream of said detection site, and
    (e)a diffusively bound polyanion for neutralizing the polycation downstream of said bound polycation and upstream of said detection site;
    contacting said application site with said blood sample; and
    detecting the presence of *Treponema pallidum* in said blood sample.

* * * * *